United States Patent
Su et al.

(10) Patent No.: US 12,281,107 B2
(45) Date of Patent: Apr. 22, 2025

(54) SET8 LYSINE METHYLTRANSFERASE INHIBITOR AND PREPARATION METHOD AND APPLICATION THEREOF

(71) Applicant: HAINAN YILING MEDICAL INDUSTRY & DEVELOPMENT Co., Ltd., Qionghai (CN)

(72) Inventors: Xueming Su, Qionghai (CN); Wei Li, Qionghai (CN); Chao Yang, Qionghai (CN)

(73) Assignee: Hainan Yiling Medical Industry & Development Co., Ltd., Qionghai (CN)

( * ) Notice: Subject to any disclaimer, the term of this patent is extended or adjusted under 35 U.S.C. 154(b) by 1104 days.

(21) Appl. No.: 16/972,454

(22) PCT Filed: Dec. 5, 2019

(86) PCT No.: PCT/CN2019/123383
§ 371 (c)(1),
(2) Date: Dec. 4, 2020

(87) PCT Pub. No.: WO2021/082181
PCT Pub. Date: May 6, 2021

(65) Prior Publication Data
US 2021/0363138 A1   Nov. 25, 2021

(30) Foreign Application Priority Data
Nov. 1, 2019 (CN) .......................... 201911060493.7

(51) Int. Cl.
C07D 249/08 (2006.01)
C07D 401/04 (2006.01)
C07D 405/14 (2006.01)
C07D 413/04 (2006.01)
C07D 413/14 (2006.01)

(52) U.S. Cl.
CPC ......... C07D 413/14 (2013.01); C07D 249/08 (2013.01); C07D 401/04 (2013.01); C07D 405/14 (2013.01); C07D 413/04 (2013.01); C07B 2200/07 (2013.01)

(58) Field of Classification Search
CPC .. C07D 413/14; C07D 249/08; C07D 401/04; C07D 405/14; C07D 413/04
See application file for complete search history.

(56) References Cited

U.S. PATENT DOCUMENTS 2,800,486 A * 7/1957 Grundmann ......... C07D 249/08
548/269.2

FOREIGN PATENT DOCUMENTS

| CN | 107827776 A | 3/2018 |
|---|---|---|
| CN | 109790148 A | 5/2019 |
| CN | 110655514 A | 1/2020 |
| CN | 110684022 A | 1/2020 |
| CN | 110759891 A | 2/2020 |
| CN | 110759902 A | 2/2020 |
| DE | 236090 A * | 5/1986 |
| WO | 2017140743 A1 | 8/2017 |

OTHER PUBLICATIONS

Conde et al. Synthesis, 1974, Issue 1, p. 28-29 (Year: 1974).*
Shine et al. J. Org. Chem., 1988, vol. 53, p. 4349-4353 (Year: 1988).*
Chen et al. Org. Lett., 2016, vol. 18, p. 1334-1337 (Year: 2016).*
Paulvannan et al. Tetrahedron, 2000, vol. 56, p. 8071-8076 (Year: 2000).*
Jagerovic et al. J. Med. Chem., 2004, vol. 47, p. 2939-2942 & Supplemental Information p. S2-S13 (Year: 2004).*
Curtis (Science of Synthesis, 2004, vol. 13, pp. 603-639) (Year: 2004).*
Shi et al. (J. Am. Chem. Soc., 2015, vol. 137, p. 5670-5673 & Supplemental Information p. S1-S112) (Year: 2015).*
Whitfield et al. J. Heterocyclic Chem., 1981, vol. 18, p. 1197-1201 (Year: 1981).*

* cited by examiner

Primary Examiner — James D. Anderson
(74) Attorney, Agent, or Firm — Craft Chu PLLC; Andrew W. Chu

(57) ABSTRACT

The present invention provides an SET8 lysine methyltransferase inhibitor and a preparation method and application thereof. The structural formula of the inhibitor is as follows:

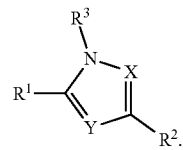

Formula I

The inhibitor provided by the present invention has a significant inhibiting effect on lysine methyltransferase SET8 and the proliferation of tumor cells.

2 Claims, No Drawings

SET8 LYSINE METHYLTRANSFERASE INHIBITOR AND PREPARATION METHOD AND APPLICATION THEREOF

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention belongs to the field of medical chemistry, and particularly relates to an SET8 lysine methyltransferase inhibitor and a preparation method and application thereof.

2. Description of Related Art Including Information Disclosed Under 37 CFR 1.97 and 37 CFR 1.98

Epigenetics is that the change of gene expression does not depend on the change of gene sequence, but on DNA methylation and histone chemical modification. The human health and diseases are affected by genetic mutations, epigenetic mutations, lifestyle and environmental factors. The mutations of epigenetic regulation coding genes are mainly reflected in histone modification change, DNA promoter hypermethylation, DNA global hypomethylation, and chromatin structure abnormality in the process of tumorigenesis and tumor development. DNA aberrant methylation may cause cancer suppressor gene transcription inhibition, genome instability and abnormal oncogene activation. Mutations of histone-modifying enzymes in tumors, including mutations of histone methylase, demethylase and acetylase, may also cause abnormal gene expression so as to determine the phenotype of tumor cells. The epigenetic changes are directly related to growth, immune escape, metastasis, heterogeneity and drug resistance of tumor cells, and even lead to tumorigenesis. The treatment strategy for epigenetic mutations becomes a new direction of tumor treatment, and clinical trials have been conducted on a variety of epigenetic drugs. In addition, the treatment strategy also has great application prospects in autoimmunity, cardiovascular disease, neurology, development and aging.

SET8 lysine methyltransferase is also called SETD8, PR-SET7 or KMT5a, and is the only lysine methyltransferase found to be able to specifically monomethylate histone $H_4$ lysine20 ($H_4K_{20}$). SET8 participates in biological processes such as gene transcription regulation, genome stability, cell cycle progression and embryonic development in the body through histone methylated modification. At present, various studies at home and abroad have reported the mechanism of SET8 lysine methyltransferase in regulating tumorigenesis and tumor development. For example, studies show that SET8 can regulate the apoptosis and proliferation of cells by methylating non-histone proteins Numb. Li et al. find that SET8 lysine methyltransferase is the conductive medium of a Wnt signal pathway and is essential for activating Wnt reporter genes and target genes in mammalian cells and zebra fish. Chen et al. find that the research hotspot miRNA regulates cell proliferation and cell cycle by directly targeting SET8. SET8 not only participates in the regulation of Wnt target gene expression and affects Wnt3a-mediated embryonic development, but also participates in the Twist regulation of epithelial-mesenchymal transition, thereby affecting tumor formation and development. In 2016, Moreaux et al. demonstrate the importance of SET8 for the survival of multiple myeloma cells for the first time, and propose that the inhibition of SET8 lysine methyltransferase is a potential strategy to improve the treatment of multiple myeloma. In addition, other studies point out that the expression of SET8 is an independent prognostic marker for patients with gastric cancer, and the expression level of SET8 lysine methyltransferase can help patients determine the risk of adverse diseases. In conclusion, SET8 lysine methyltransferase plays an important role in the life process of the body, participates in the regulation of the cell cycle, cell proliferation and apoptosis of cells in the body, and is closely related to the occurrence, growth and metastasis of tumors. However, the reports on compounds targeting SET8 lysine methyltransferase are fewer. Therefore, the research of a new kind of compounds targeting SET8 lysine methyltransferase is a difficult point and hot spot in the current research.

BRIEF SUMMARY OF THE INVENTION

In order to solve the technical problems in the prior art, the present invention develops a new SET8 lysine methyltransferase inhibitor and a preparation method and application thereof.

One of the technical solutions of the present invention provides an SET8 lysine methyltransferase inhibitor shown in formula I and optical isomer, solvate or pharmaceutically acceptable salt thereof, formula I

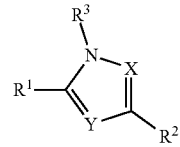

wherein
X and Y are independently selected from CH or N.
$R^1$, $R^2$ or $R^3$ is independently selected from hydrogen, $C_1$-$C_6$ alkyl, substituted $C_1$-$C_6$ alkyl, cycloalkyl, substituted cycloalkyl, phenyl, substituted phenyl, benzyl, substituted benzyl, heterocyclic radical or substituted heterocyclic radical; the substituted $C_1$-$C_6$ alkyl is independently substituted by one or more substituents selected from halogen, nitro, amino, hydroxyl or cyano; the substituted cycloalkyl, the substituted phenyl or the substituted benzyl is independently substituted by one or more substituents selected from halogen, $C_1$-$C_6$ alkyl, $C_1$-$C_6$ alkoxy, trifluoromethoxy, trifluoromethyl, nitro, amino, hydroxyl, $C_1$-$C_6$ alkanoylamino, cyano, $C_1$-$C_6$ alkylamino or $C_1$-$C_6$ alkoxy acyl; and the substituted heterocyclic radical is independently substituted by one or more substituents selected from halogen, $C_1$-$C_6$ alkyl, $C_1$-$C_6$ alkoxy, trifluoromethoxy, trifluoromethyl, phenyl, benzyl, nitro, amino, hydroxyl, $C_1$-$C_6$ alkanoylamino, cyano, $C_1$-$C_6$ alkylamino or $C_1$-$C_6$ alkoxy acyl.

In a further improved solution, X and Y are both N.

In the further improved solution, $R^1$ is selected from $C_1$-$C_4$ alkyl, substituted $C_1$-$C_4$ alkyl, $C_5$-$C_8$ cycloalkyl, heterocyclic radical or substituted heterocyclic radical; the substituted $C_1$-$C_4$ alkyl is independently substituted by one or more substituents selected from halogen, nitro, amino or cyano; and the substituted heterocyclic radical is independently substituted by one or more substituents selected from $C_1$-$C_4$ alkyl or benzyl.

Preferably, $R^2$ is selected from phenyl, substituted phenyl, benzyl or substituted benzyl; and the substituted phenyl or the substituted benzyl is independently substituted by one or more substituents selected from $C_1$-$C_4$ alkyl or $C_1$-$C_4$ alkoxy.

Preferably, $R^3$ is selected from $C_1$-$C_4$ alkyl, $C_5$-$C_8$ cycloalkyl, phenyl, substituted phenyl, benzyl, substituted benzyl, heterocyclic radical or substituted heterocyclic radical; the substituted phenyl or the substituted benzyl is independently substituted by one or more substituents selected from $C_1$-$C_4$ alkyl or $C_1$-$C_4$ alkoxy; and the substituted heterocyclic radical is independently substituted by one or more substituents selected from $C_1$-$C_4$ alkyl.

In the further improved solution, $R^1$ is selected from $C_1$-$C_4$ alkyl, substituted $C_1$-$C_4$ alkyl, ch cyclohexyl, heterocyclic radical or substituted heterocyclic radical; the substituted $C_1$-$C_4$ alkyl is independently substituted by one amino; the substituted heterocyclic radical is independently substituted by one substituent selected from $C_1$-$C_4$ alkyl or benzyl; and the heterocyclic radical is morpholinyl or tetrahydropyranyl.

In the further improved solution, $R^3$ is selected from $C_1$-$C_4$ alkyl, ch cyclohexyl, phenyl, substituted phenyl, benzyl, substituted benzyl, heterocyclic radical or substituted heterocyclic radical; the substituted phenyl or the substituted heterocyclic radical is independently substituted by one $C_1$-$C_4$ alkyl, and the substituted benzyl is substituted by one $C_1$-$C_4$ alkoxy; and the heterocyclic radical is selected from pyrazinyl, piperidyl or pyridyl.

In the further improved solution, $R^1$ is selected from methyl, heterocyclic radical or substituted heterocyclic radical; the substituted heterocyclic radical is substituted by one benzyl; and the heterocyclic radical is morpholinyl or tetrahydropyranyl.

Preferably, $R^2$ is selected from phenyl, substituted phenyl, benzyl or substituted benzyl; the substituted phenyl is substituted by one methyl; and the substituted benzyl is substituted by one methoxyl.

Preferably, $R^3$ is selected from methyl, ch cyclohexyl, phenyl, substituted phenyl, benzyl, substituted benzyl, heterocyclic radical or substituted heterocyclic radical; the substituted phenyl or the substituted heterocyclic radical is independently substituted by one methyl; the substituted benzyl is substituted by one methoxyl; and the heterocyclic radical is selected from pyrazinyl, piperidyl or pyridyl.

In the further improved solution, the inhibitor shown in formula I is selected from the following compounds:

1): 2-(3-(4-methoxybenzyl)-1-(1-methylpiperidin-4-yl)-1H-1,2,4-triazol-5-yl) morpholine;
2): 2-(1,3-bis(4-methoxybenzyl)-1H-1,2,4-triazol-5-yl)morpholine;
3): 2-(1-cyclohexyl-3-(4-methoxybenzyl)-1H-1,2,4-triazol-5-yl)morpholine;
4): 2-(3-(4-methoxybenzyl)-1-phenyl-1H-1,2,4-triazol-5-yl) morpholine;
5): 2-(3-(4-methoxybenzyl)-1-(m-methylphenyl)-1H-1,2,4-triazol-5-yl)morpholine;
6): 2-(3-(4-methoxybenzyl)-1-(pyridin-2-yl)-1H-1,2,4-triazol-5-yl)morpholine;
7): 2-(3-(4-methoxybenzyl)-1-(pyrazin-2-yl)-1H-1,2,4-triazol-5-yl)morpholine;
8): 2-(3-(4-methoxybenzyl)-1-methyl-1H-1,2,4-triazol-5-yl) morpholine;
9): 4-benzyl-2-(3-(4-methoxybenzyl)-1-(1-methylpiperidin-4-yl)-1H-1,2,4-triazol-5-yl)morpholine;
10): 4-(3-(4-methoxybenzyl)-5-(tetrahydro-2H-pyran-2-yl)-1H-1,2,4-triazol-5-yl)-1-methylpiperidin;
11): 3-(4-methoxybenzyl)-1-(1-methylpiperidin-4-yl)-1H-1,2,4-triazol-5-yl)methylamine;
12): 1,3-bis(4-methoxybenzyl)-5-(tetrahydro-2H-pyran-2-yl)-1H-1,2,4-triazole;
13): 2-(1-(4-methoxybenzyl)-3-phenyl-1H-1,2,4-triazol-5-yl)morpholine;
14): 2-(3-benzyl-1-(1-methylpiperidin-4-yl)-1H-1,2,4-triazol-5-yl)morpholine;
15): 2-(1-(1-methylpiperidin-4-yl)-3-phenyl-1H-1,2,4-triazol-5-yl)morpholine;
16): 2-(1-(1-methylpiperidin-4-yl)-3-(p-methylphenyl)-1H-1,2,4-triazol-5-yl)morpholine;
17): 2-(1-(1-methylpiperidin-4-yl)-3-(m-methylphenyl)-1H-1,2,4-triazol-5-yl)morpholine;
18): 4-(5-cyclohexyl-3-(4-methoxybenzyl)-1H-1,2,4-triazol-5-yl)-1-methylpiperidin;
19): 4-(5-(tert-butyl)-3-(4-methoxybenzyl)-1H-1,2,4-triazol-5-yl)-1-methylpiperidin;
20): 4-(3-(4-methoxybenzyl)-5-methyl-1H-1,2,4-triazol-5-yl)-1-methylpiperidin;
21): 5-cyclohexyl-1,3-dis(4-methoxybenzyl)-1H-1,2,4-triazole.

Explanation of Terms

The term "halogen" used in the present invention includes but is not limited to fluorine, chlorine, bromine and the like.

The term "alkyl" used in the present invention means straight or branched saturated hydrocarbyl such as $C_1$-$C_{10}$ alkyl, $C_1$-$C_6$ alkyl or $C_1$-$C_4$ alkyl. The non-limiting embodiments of alkyl include methyl, ethyl, propyl, isopropyl, butyl and the like.

The term "alkoxy" used in the present invention means a group having "W—O—" structure, where W is alkyl such as $C_1$-$C_{10}$ alkoxy, $C_1$-$C_6$ alkoxy or $C_1$-$C_4$ alkoxy, and the non-limiting embodiments of alkoxy comprises methoxyl, ethoxy, propoxy, isopropoxy, tert-butoxy and the like.

The term "cycloalkyl" used in the present invention means saturated or partially saturated cyclic hydrocarbyl, and the number of carbon atoms constituting the cycloalkyl can be 3-15, for example, 3-10. The specific examples include but are not limited to cyclopropanyl, cyclobutanyl, cyclopentyl, ch cyclohexyl, cycloheptyl and the like.

The term "heterocyclic radical" used in the present invention means that in addition to carbon atoms, the atoms constituting the ring also contain at least one heteroatom selected from N, O or S, and the specific examples include but are not limited to tetrahydrofuranyl, tetrahydropyranyl, piperidyl, piperazinyl, pyrrolyl, thienyl, isoxazolyl, oxazolyl, imidazolyl, thiazolyl, pyridyl, pyrimidinyl, piperidyl, triazinyl, morpholinyl, thiadiazole and the like.

Another solution of the present invention provides a preparation method of an SET8 lysine methyltransferase inhibitor shown in formula I and optical isomer, solvate or pharmaceutically acceptable salt thereof, comprising the following steps:

1) The carboxylic acid shown in formula A or the acyl chloride shown in formula D and the thioamide shown in formula B are subjected to condensation reaction in the presence of catalysts to produce a thioimide intermediate shown in formula C;
2) The thioimide intermediate shown in formula C and the hydrazine shown in formula E or the salt thereof are cyclized under the catalysis of a base to produce the SET8 lysine methyltransferase inhibitor shown in formula 1;

A reaction equation is as follows:

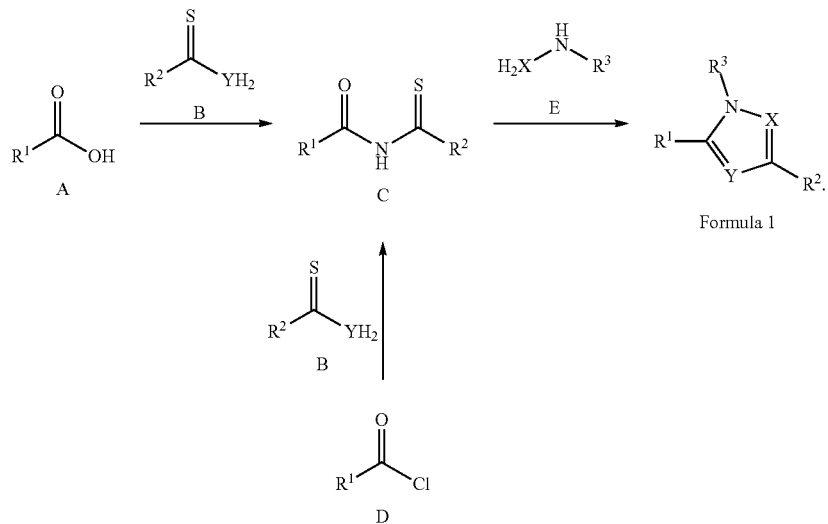

Formula 1

In the further improved solution, the catalysts in step 1) are HATU and DIEA or pyridine and 4-dimethylaminopyridine, wherein the molar ratio of the carboxylic acid shown in formula A or the acyl chloride shown in formula D to the thioamide shown in formula B to HATU to DIEA is 1:1.05-1.2:1.05-1.2:1.05-1.2.

Preferably, the base in step 2) is sodium acetate; and the molar ratio of the thioimide intermediate shown in formula C to the hydrazine shown in formula E or the salt thereof to the base is 1:1.1-1.3:1.25-2.6.

In the further improved solution, the reaction solvent shown in step 2) is a mixture of acetic acid and 1,4-dioxane in a volume ratio of 1:0.8-2.

Another aspect of the present invention provides a pharmaceutical composition which comprises an SET8 lysine methyltransferase inhibitor shown in formula I and optical isomer, solvate or pharmaceutically acceptable salt and pharmaceutically acceptable carrier or excipient thereof.

The pharmaceutical composition can be administered by the following routes: locally, intravenously, orally, subcutaneously and the like; and can be prepared into various appropriate dosage forms according to the administration route. In the case of oral administration, the compound of the present invention can be prepared into any orally acceptable dosage form, including but not limited to tablets, capsules and granules. The carrier or excipient includes but is not limited to lactose, glucose and microcrystalline cellulose as fillers; carboxymethyl cellulose, povidone and methyl cellulose as adhesives; sodium carboxymethylcellulose and polyvinylpolypyrrolidone as disintegrants; and magnesium stearate, talcum powder and silicon dioxide as lubricants. When applied topically to the skin, the compound of the present invention can be prepared into an appropriate dosage forms such as ointment, and the carrier or excipient is selected from petrolatum, propylene glycol, polyethylene oxide and the like.

The SET8 lysine methyltransferase inhibitor shown in formula I and optical isomer, solvate or pharmaceutically acceptable salt thereof can be used for treatment of tumors such as liver cancer, glioma, colorectal cancer, gastric cancer, breast cancer, melanoma, lung cancer, prostatic cancer, pancreatic cancer, bladder cancer, kidney cancer, multiple myeloma and cervical cancer.

The present invention is the first to synthesize and identify an SET8 lysine methyltransferase inhibitor. The evaluation results of in vitro activity show that the inhibitor has significant inhibitory activity on SET8 lysine methyltransferase and significant in vitro anti-tumor activity as well as low toxicity, and can be further developed into a targeted anti-tumor drug targeting SET8 lysine methyltransferase.

BRIEF DESCRIPTION OF THE SEVERAL VIEWS OF THE DRAWINGS

None.

DETAILED DESCRIPTION OF THE INVENTION

The implementation solution of the present invention will be described below in detail in combination with the embodiments. However, those skilled in the art will understand that the following embodiments are only used for describing the present invention and should not be regarded as the limitation to the scope of the present invention. Experimental methods in which specific conditions are not specified in the embodiment are carried out under conventional conditions or as recommended by the manufacturer. The reagents or instruments used of which the manufacturers are not specified are all conventional products that can be purchased commercially. When the amount or yield of each substance is calculated, part of data is carried.

Embodiment 1 Preparing 2-(3-(4-methoxybenzyl)-1-(1-methylpiperidin-4-yl)-1H-1,2,4-triazol-5-yl)morpholine (Compound 1) Hydrochloride

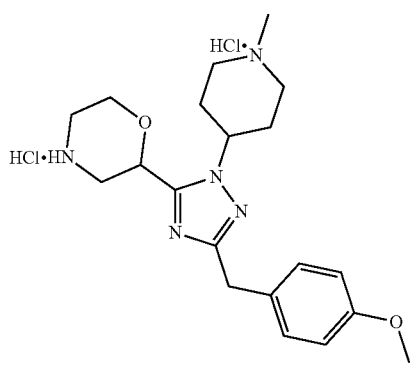

Step 1: Preparing 2-((2-(4-methoxyphenyl)ethanethioyl)carbamoyl)morpholine-4-carboxylic Acid Tert-Butyl Ester (Compound 1-3)

A reaction equation is as follows:

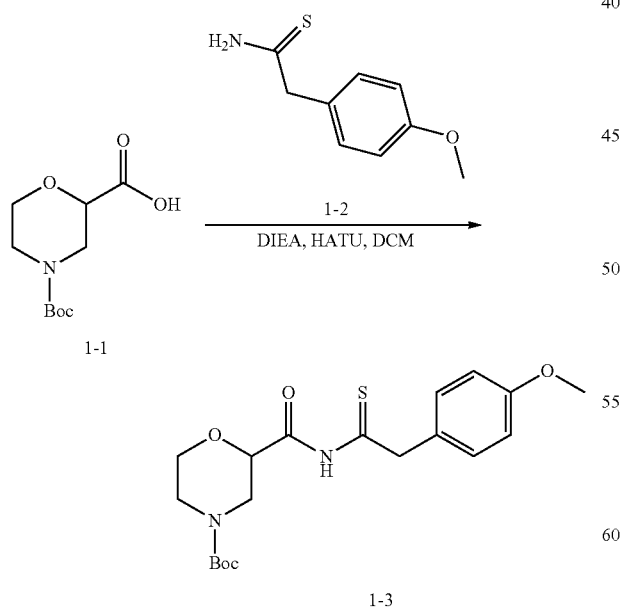

Dissolving 4-(tert-butoxycarbonyl)morpholine-2-carboxylic acid (1.0 mmol, 231 mg) shown in formula 1-1 and 2-(7-benzotriazole oxide)-N,N,N',N'-tetramethyluronium hexafluorophosphate (HATU, 1.1 mmol, 418 mg) in 4 mL of dry dichloromethane (DCM), adding 2-(4-methoxyphenyl)thioacetamide (1.1 mmol, 199 mg) shown in formula 1-2 to the above system after stirring for 20 min under the protection of nitrogen at room temperature, continuing stirring for 1 h, then dropping N,N-diisopropylethylamine (DIEA, 1.1 mmol, 142 mg) into the above reaction system, and continuing stirring for reaction for 2 days under the protection of nitrogen at room temperature; and diluting the reaction solution with 50 mL of ethyl acetate, cleaning with 20 mL of water and saturated sodium chloride solution in sequence, drying with anhydrous sodium sulfate, concentrating the reaction solution, and then carrying out column chromatography separation [V(petroleum ether):V(ethyl acetate)=5:1-2:1] to obtain 134 mg of pale yellow oil 1-3, with the yield of 34%.

$^1$H NMR (400 MHz, CDCl3): δ 10.25 (s, 1H), 7.25 (d, J=8.7 Hz, 2H), 6.85 (d, J=8.7 Hz, 2H), 4.61-4.52 (m, 2H), 4.28 (brs, 1H), 4.00-3.93 (m, 3H), 3.79 (s, 3H), 3.58 (td, J=11.8, 2.8 Hz, 1H), 2.91-2.79 (m, 2H), 1.47 (s, 9H).

Step 2: Preparing 2-(3-(4-methoxybenzyl)-1-(1-methylpiperidin-4-yl)-1H-1,2,4-triazol-5-yl)morpholine-4-carboxylic Acid Tert-Butyl Ester (Compound 1-5)

A reaction equation is as follows:

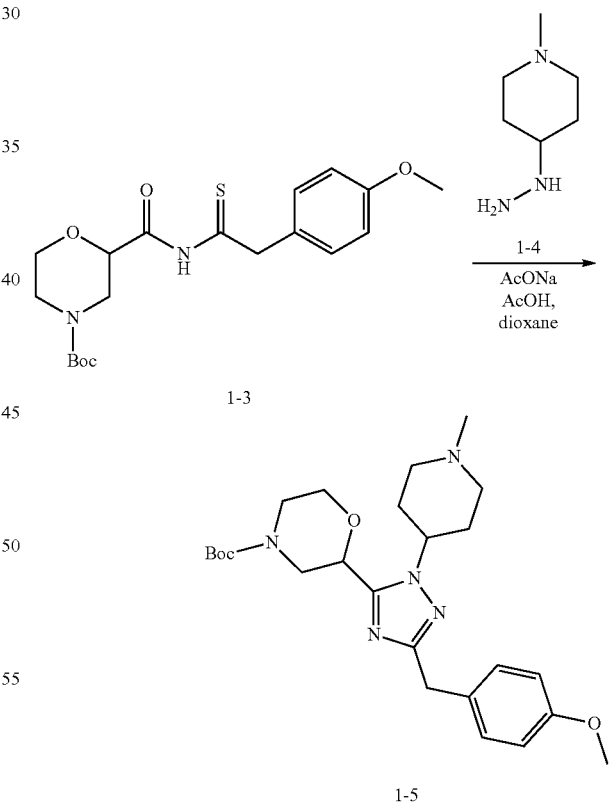

Dissolving the compound 1-3 (0.15 mmol, 59 mg), 4-hydrazino-1-methylpiperidine (0.18 mmol, 23 mg) shown in formula 1-4, and sodium acetate (0.195 mmol, 16 mg) in a mixed solvent of 1 mL of acetic acid and 1 mL of 1,4-dioxane, then sealing, and heating at 80° C. for reaction till the complete reaction of the compound 1-3; and diluting the reaction solution with 30 mL of ethyl acetate, cleaning with 20 mL of saturated sodium carbonate solution and saturated sodium chloride solution in sequence, drying with anhydrous sodium sulfate, concentrating the reaction solution, and then carrying out column chromatography separation [V(dichloromethane solution of ammonia):V(methanol) =25:1-20:1] to obtain 63 mg of pale yellow oil 1-5, with the yield of 89%.

Step 3: Preparing 2-(3-(4-methoxybenzyl)-1-(1-methylpiperidin-4-yl)-1H-1,2,4-triazol-5-yl)morpholine (Compound 1) Hydrochloride A reaction equation is as follows:

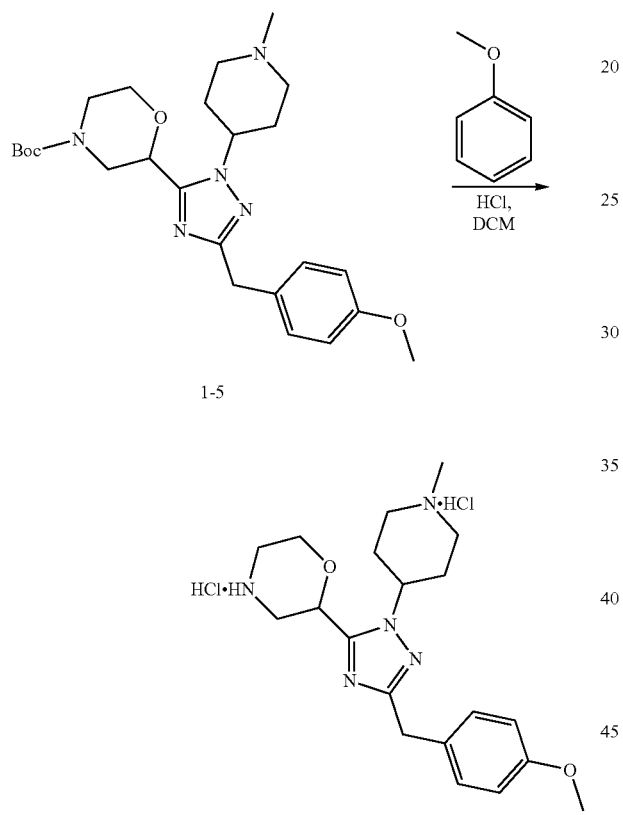

Dissolving the compound 1-5 (0.13 mmol, 61 mg), anisole (0.13 mmol, 14 mg) and 0.4 mL of 1,4-dioxane solution (4M) of hydrogen chloride in 3 mL of dichloromethane, and sealing for reaction for 2 days till the complete reaction of the compound 1-5. Evaporating the reaction solution to dryness to obtain a white solid, cleaning the solid with a mixed solvent of 10 mL of petroleum ether and ethyl acetate (3:1) for three times, and then draining to obtain 50 mg of white solid 1, with the yield of 87%.

$^1$H NMR (400 MHz, CD$_3$OD) δ 7.18-7.16 (m, 2H), 6.85-6.82 (m, 2H), 5.48-5.45 (m, 1H), 5.04-4.99 (m, 1H), 4.22-4.13 (m, 2H), 4.00 (s, 2H), 3.75 (s, 3H), 3.69-3.52 (m, 6H), 3.42-3.35 (m, 3H), 2.94 (s, 3H), 2.53-2.23 (m, 5H). $^{13}$C NMR (400 MHz, CD$_3$OD): δ 162.7, 160.1, 151.9, 130.9, 130.8, 130.4, 130.1, 115.0, 68.1, 67.2, 64.8, 55.7, 54.3, 54.3, 54.2, 45.6, 43.9, 33.8, 30.9, 30.2. ESI-MS: m/z 372.1 [M+H]$^+$.

Embodiment 2 Preparing 2-(1,3-bis(4-methoxybenzyl)-1H-1,2,4-triazol-5-yl)morpholine (Compound 2)

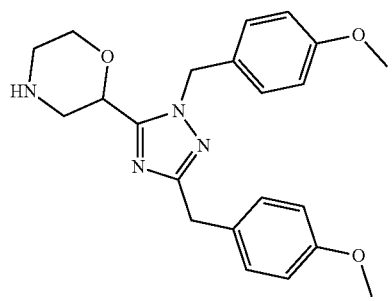 [SMILES: COc1ccc(Cc2nc(C3CNCCO3)n(Cc3ccc(OC)cc3)n2)cc1]

Step 1: Preparing 2-(1,3-bis(4-methoxybenzyl)-1H-1,2,4-triazol-5-yl)morpholine-4-carboxylic Acid Tert-Butyl Ester (Compound 2-1)

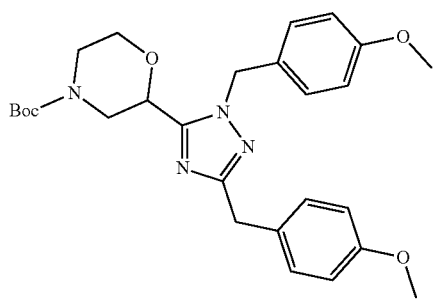

2-1

Dissolving the compound 1-3 (0.15 mmol, 59 mg), (4-methoxybenzyl) hydrazine dihydrochloride (0.18 mmol, 34 mg), and sodium acetate (0.36 mmol, 30 mg) in a mixed solvent of 1 mL of acetic acid and 1 mL of 1,4-dioxane, then sealing, and heating at 80° C. for reaction till the complete reaction of the compound 1-3. Diluting the reaction solution with 30 mL of ethyl acetate, cleaning with 20 mL of sodium carbonate solution and saturated sodium chloride solution in sequence, drying with anhydrous sodium sulfate, conducting concentration, and then carrying out column chromatography separation [V(petroleum ether):V(ethyl acetate)=3:1-1:1] to obtain 50 mg of pale yellow oil 2-1, with the yield of 68%.

$^1$H NMR (400 MHz, CDCl$_3$): δ 7.25-7.16 (m, 4H), 6.87-6.82 (m, 4H), 5.32 (s, 2H), 4.43 (dd, J=10.5, 2.2 Hz, 1H), 4.22-4.06 (m, 1H), 3.99 (s, 3H), 3.79 (s, 3H), 3.78 (s, 3H), 3.62-3.56 (m, 1H), 3.21 (t, J=11.5 Hz, 1H), 3.00 (s, 1H), 1.44 (s, 9H).

Step 2: Preparing 2-(1,3-bis(4-methoxybenzyl)-1H-1,2,4-triazol-5-yl)morpholine (Compound 2)

Dissolving the compound 2-1 (0.1 mmol, 49 mg), anisole (0.1 mmol, 11 mg) and 0.5 mL of 1,4-dioxane solution (4M) of hydrogen chloride in 3 mL of dichloromethane, and sealing for reaction for 3 days till the complete reaction of the compound 2-1. Evaporating the reaction solution to dryness to obtain yellow oil, diluting the yellow oil with 30 mL of ethyl acetate, cleaning with 20 mL of saturated sodium carbonate solution, drying with anhydrous sodium sulfate, conducting concentration, and then carrying out column chromatography separation [V(dichloromethane solution of ammonia):V(methanol)=25:1-20:1] to obtain 26 mg of yellow oil 2, with the yield of 66%.

$^1$H NMR (400 MHz, CDCl$_3$): δ 7.26-7.17 (m, 4H), 6.86-6.81 (m, 4H), 5.38-5.29 (m, 2H), 4.57-4.54 (m, 1H), 3.98 (s, 2H), 3.88-3.84 (m, 1H), 3.78 (s, 3H), 3.77 (s, 3H), 3.68-3.62 (m, 1H), 3.17-3.10 (m, 2H), 2.97-2.84 (m, 2H). $^{13}$C NMR (400 MHz, CDCl3): δ 162.3, 159.6, 158.3, 153.1, 130.6, 130.0, 129.2, 128.1, 114.3, 114.0, 70.8, 67.6, 55.5, 55.46, 52.4, 48.8, 45.6, 34.0. ESI-MS: m/z 395.2 [M+H]$^+$.

Embodiment 3 Preparing 2-(1-cyclohexyl-3-(4-methoxybenzyl)-1H-1,2,4-triazol-5-yl)morpholine (Compound 3)

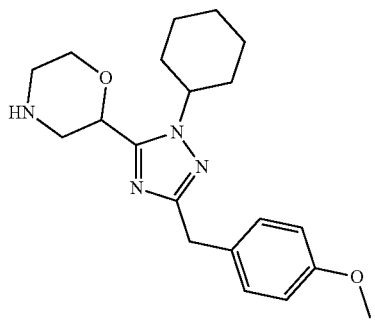 [SMILES: COc1ccc(Cc2nc(C3CNCCO3)n(C3CCCCC3)n2)cc1]

Step 1: Preparing 2-(1-cyclohexyl-3-(4-methoxy-benzyl)-1H-1,2,4-triazol-5-yl)morpholine-4-carboxylic Acid Tert-Butyl Ester (Compound 3-1)

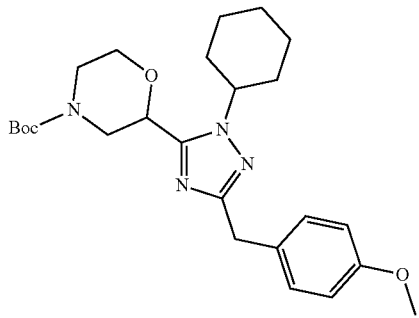

3-1

Dissolving the compound 1-3 (0.16 mmol, 63 mg), cyclohexylhydrazine hydrochloride (0.2 mmol, 30 mg), and sodium acetate (0.36 mmol, 30 mg) in a mixed solvent of 1 mL of acetic acid and 1 mL of 1,4-dioxane, then sealing, and heating at 80° C. for reaction till the complete reaction of the compound 1-3. Diluting the reaction solution with 30 mL of ethyl acetate, cleaning with 20 mL of sodium carbonate solution and saturated sodium chloride solution in sequence, drying with anhydrous sodium sulfate, concentrating the reaction solution, and then carrying out column chromatography separation [V(petroleum ether):V(ethyl acetate)=3:1-1:1] to obtain 40 mg of pale yellow oil 3-1, with the yield of 55%.

Step 2: Preparing 2-(1-cyclohexyl-3-(4-methoxy-benzyl)-1H-1,2,4-triazol-5-yl)morpholine (Compound 3)

Dissolving the compound 3-1 (0.09 mmol, 41 mg), anisole (0.1 mmol, 11 mg) and 0.5 mL of 1,4-dioxane solution (4M) of hydrogen chloride in 3 mL of dichloromethane, and sealing for reaction for 3 days till the complete reaction of the compound 3-1. Evaporating the reaction solution to dryness to obtain yellow oil, diluting the yellow oil with 30 mL of ethyl acetate, cleaning with 20 mL of saturated sodium carbonate solution, drying with anhydrous sodium sulfate, concentrating the reaction solution, and then carrying out column chromatography separation [V(dichloromethane solution of ammonia):V(methanol)=25:1-20:1] to obtain 26 mg of yellow oil 3, with the yield of 81%.

$^1$H NMR (400 MHz, CDCl3): δ 7.25-7.23 (m, 2H), 6.82-6.80 (m, 2H), 4.67-4.64 (m, 2H), 4.28-4.21 (m, 2H), 3.98 (s, 2H), 3.85-3.79 (m, 1H), 3.77 (s, 3H), 3.73-3.67 (m, 1H), 3.31-3.25 (m, 1H), 3.19-3.15 (m, 1H), 3.01-2.87 (m, 2H), 1.98-2.85 (m, 6H), 1.73-1.70 (m, 1H), 1.40-1.26 (m, 4H). $^{13}$C NMR (400 MHz, CDCl3): δ 161.8, 158.1, 152.0, 130.7, 129.9, 113.8, 70.0, 67.4, 58.0, 55.3, 48.9, 45.6, 33.9, 33.0, 32.9, 25.7, 25.1. ESI-MS: m/z 357.2 [M+H]$^+$.

Embodiment 4 Preparing 2-(3-(4-methoxybenzyl)-1-phenyl-1H-1,2,4-triazol-5-yl)morpholine (Compound 4) Hydrochloride

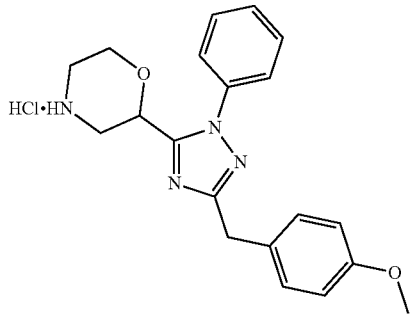

According to the method of embodiment 1, making the compound 1-3 react with phenylhydrazine to prepare an intermediate product (75 mg, with the yield of 76%), and then removing the tert-butoxycarbonyl protection group with the 1,4-dioxane solution of hydrogen chloride to prepare compound 4 hydrochloride (30 mg, with the yield of 77%), white solid powder.

$^1$H NMR (400 MHz, CD3OD) δ 9.33 (brs, 1H), 7.62-7.59 (m, 5H), 7.25-7.23 (m, 2H), 6.88-6.86 (m, 2H), 4.89-4.87 (m, 1H), 4.00 (s, 3H), 3.83-3.81 (m, 2H), 3.72 (s, 2H), 3.50 (s, 2H), 3.24-3.18 (m, 2H). $^{13}$C NMR (400 MHz, CD3OD): 5164.1, 159.5, 151.8, 130.9, 130.7, 130.3, 125.8, 124.9, 123.4, 115.0, 66.5, 64.3, 55.7, 45.6, 42.8, 34.0. ESI-MS: m/z 351.1 [M+H]$^+$.

Embodiment 5 Preparing 2-(3-(4-methoxybenzyl)-1-(m-methylphenyl)-1H-1,2,4-triazol-5-yl)morpholine (Compound 5) Hydrochloride

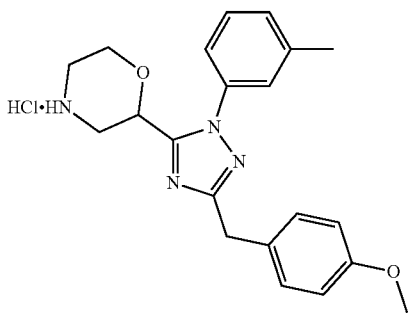

According to the method of embodiment 1, making the compound 1-3 react with 3-tolylhydrazine to prepare an intermediate product (80 mg, with the yield of 78%), and then removing the tert-butoxycarbonyl protection group with the 1,4-dioxane solution of hydrogen chloride to prepare compound 5 hydrochloride (32 mg, with the yield of 75%), white solid powder.

$^1$H NMR (400 MHz, CD3OD) δ 9.43 (brs, 1H), 7.57-7.48 (m, 4H), 7.24-7.22 (m, 2H), 6.87-6.86 (m, 2H), 4.89-4.86 (m, 1H), 4.01 (s, 3H), 3.82-3.81 (m, 2H), 3.72 (s, 2H), 3.48 (s, 2H), 3.22-3.19 (m, 2H), 2.43 (m, 3H). $^{13}$C NMR (400 MHz, CD3OD): δ 164.5, 160.0, 152.2, 141.3, 137.8, 131.4, 130.84, 130.82, 130.6, 126.3, 122.8, 114.9, 66.8, 64.1, 55.7, 45.7, 43.9, 34.3, 21.3. ESI-MS: m/z 365.1 [M+H]$^+$.

Embodiment 6 Preparing 2-(3-(4-methoxybenzyl)-1-(pyridin-2-yl)-1H-1,2,4-triazol-5-yl)morpholine (Compound 6)

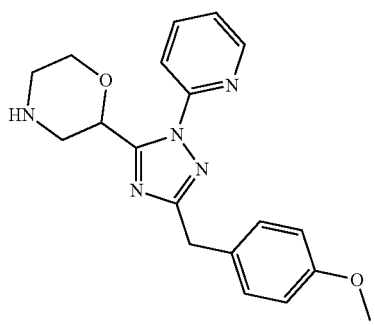 [SMILES: COc1ccc(Cc2nc(C3CNCCO3)n(-c3ccccn3)n2)cc1]

According to the method of embodiment 1, making the compound 1-3 react with 2-hydrazinopyridine to prepare an intermediate product (25 mg, with the yield of 44%), and then removing the tert-butoxycarbonyl protection group with the 1,4-dioxane solution of hydrogen chloride to prepare compound 6 (18 mg, with the yield of 90%), pale yellow oil.

$^1$H NMR (400 MHz, CDCl$_3$): δ 8.49 (d, J=4.9 Hz, 1H), 7.83 (d, J=2.7 Hz, 2H), 7.32-7.27 (m, 3H), 6.84 (d, J=8.6 Hz, 2H), 5.56 (dd, J=9.3, 2.4 Hz, 1H), 5.30 (s, 3H), 4.09 (s, 2H), 4.01 (d, J=11.4 Hz, 1H), 3.86-3.67 (m, 4H), 3.43 (dd, J=12.3, 1.8 Hz, 1H), 3.12 (ddd, J=18.7, 13.2, 6.3 Hz, 2H), 2.90 (d, J=12.6 Hz, 1H). $^{13}$C NMR (400 MHz, CDCl3): δ 163.2, 158.2, 154.7, 150.7, 148.0, 138.8, 129.9, 122.6, 116.4, 113.8, 71.9, 67.9, 55.2, 53.4, 49.2, 45.2, 33.8, 29.8. ESI-MS: m/z 352.2 [M+H]$^+$.

Embodiment 7 Preparing 2-(3-(4-methoxybenzyl)-1-(pyrazin-2-yl)-1H-1,2,4-triazol-5-yl)morpholine (Compound 7)

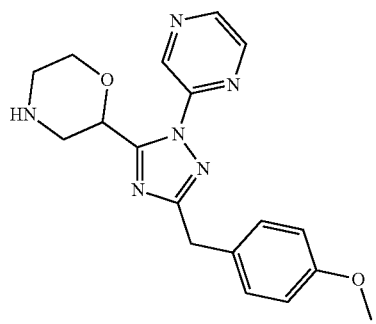 [SMILES: COc1ccc(Cc2nc(C3CNCCO3)n(-c3cnccn3)n2)cc1]

According to the method of embodiment 1, making the compound 1-3 react with 2-hydrazinopyrazine to prepare an intermediate product (36 mg, with the yield of 63%), and then removing the tert-butoxycarbonyl protection group with the 1,4-dioxane solution of hydrogen chloride to prepare compound 7 (20 mg, with the yield of 71%), pale yellow oil.

$^1$H NMR (400 MHz, CDCl$_3$): δ 9.20 (s, 1H), 8.57 (d, J=2.5 Hz, 1H), 8.45 (s, 1H), 7.35-7.25 (m, 2H), 6.85 (t, J=5.7 Hz, 2H), 5.47 (dd, J=9.2, 2.6 Hz, 1H), 4.10 (s, 2H), 3.97 (dt, J=11.4, 2.6 Hz, 1H), 3.81-3.66 (m, 4H), 3.36 (dd, J=12.3, 2.4 Hz, 1H), 3.23-3.02 (m, 2H), 2.90 (d, J=12.6 Hz, 1H). $^{13}$C NMR (400 MHz, CDCl3): δ 164.0, 158.3, 155.6, 146.9, 142.9, 141.6, 138.7, 129.9, 129.4, 113.8, 71.5, 67.9, 55.2, 49.0, 45.3, 33.7, 29.6. ESI-MS: m/z 353.2 [M+H]$^+$.

Embodiment 8 Preparing 2-(3-(4-methoxybenzyl)-1-methyl-1H-1,2,4-triazol-5-yl)morpholine (Compound 8)

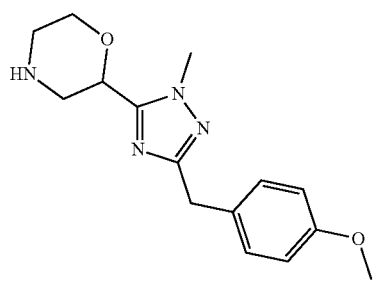 [SMILES: COc1ccc(Cc2nc(C3CNCCO3)n(C)n2)cc1]

According to the method of embodiment 1, making the compound 1-3 react with methylhydrazine sulfate to prepare an intermediate product (24 mg, with the yield of 51%), and then removing the tert-butoxycarbonyl protection group with the 1,4-dioxane solution of hydrogen chloride to prepare compound 8 (14 mg, with the yield of 80%), pale yellow oil.

$^1$H NMR (400 MHz, CDCl$_3$): δ 7.07 (d, J=8.5 Hz, 2H), 6.82 (d, J=8.6 Hz, 2H), 4.64 (dd, J=10.0, 2.7 Hz, 1H), 4.10-3.97 (m, 4H), 3.87-3.69 (m, 5H), 3.64 (s, 3H), 3.24 (dd,

J=12.5, 2.3 Hz, 1H), 3.15-2.96 (m, 2H), 2.87 (d, J=12.5 Hz, 1H). $^{13}$C NMR (400 MHz, CDCl3): δ 160.8, 158.6, 154.7, 129.3, 127.1, 114.2, 73.3, 68.1, 55.2, 49.9, 45.5, 35.4, 31.5. ESI-MS: m/z 289.1 [M+H]$^+$.

Embodiment 9 Preparing 4-benzyl-2-(3-(4-methoxybenzyl)-1-(1-methylpiperidin-4-yl)-1H-1,2,4-triazol-5-yl)morpholine (Compound 9)

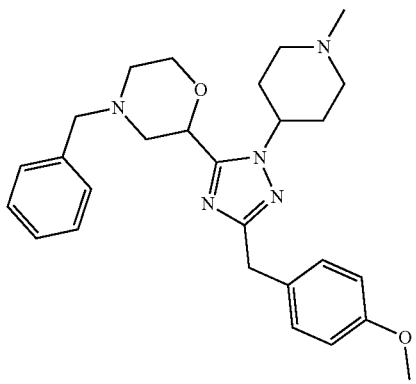 [SMILES: COc1ccc(Cc2nc(C3CN(Cc4ccccc4)CCO3)n(C3CCN(C)CC3)n2)cc1]

According to the method of embodiment 1, making 4-benzylmorpholine-2-carboxylic acid react with 2-(4-methoxyphenyl)thioacetamide shown in formula 1-2 to prepare a thioimide intermediate (20 mg, with the yield of 10%) and then react with 4-hydrazino-1-methylpiperidine to prepare compound 9 (16 mg, with the yield of 69%), pale yellow oil.

$^1$H NMR (400 MHz, CDCl$_3$): δ 7.40-7.28 (m, 5H), 7.23 (d, J=8.5 Hz, 2H), 6.80 (d, J=8.6 Hz, 2H), 4.72 (dd, J=10.4, 2.3 Hz, 1H), 4.23 (t, J=11.1 Hz, 1H), 4.03-3.91 (m, 3H), 3.87-3.74 (m, 4H), 3.58 (dd, J=26.3, 12.9 Hz, 2H), 3.07-3.01 (m, 3H), 2.74 (d, J=11.5 Hz, 1H), 2.67-2.52 (m, 1H), 2.38-2.30 (m, 4H), 2.29-2.20 (m, 2H), 2.07 (d, J=10.0 Hz, 2H), 1.91 (d, J=11.7 Hz, 1H), 1.80 (d, J=11.7 Hz, 1H). $^{13}$C NMR (400 MHz, CDCl3): δ 161.7, 158.0, 152.0, 137.5, 130.4, 129.8, 129.1, 128.3, 127.3, 113.6, 70.1, 67.3, 63.0, 56.0, 55.2, 55.0, 52.5, 46.1, 33.8, 31.9. ESI-MS: m/z 462.2 [M+H]$^+$.

Embodiment 10 Preparing 4-(3-(4-methoxybenzyl)-5-(tetrahydro-2H-pyran-2-yl)-1H-1,2,4-triazol-5-yl)-1-methylpiperidin (Compound 10)

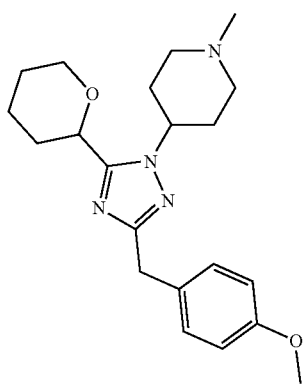 [SMILES: COc1ccc(Cc2nc(C3CCCCO3)n(C3CCN(C)CC3)n2)cc1]

According to the method of embodiment 1, making tetrahydropyran-2-carboxylic acid react with 2-(4-methoxyphenyl)thioacetamide shown in formula 1-2 to prepare a thioimide intermediate (300 mg, with the yield of 26%) and then react with 4-hydrazino-1-methylpiperidine to prepare compound 10 (33 mg, with the yield of 65%), pale yellow oil.

$^1$H NMR (400 MHz, CDCl$_3$): δ 7.24 (d, J=8.6 Hz, 2H), 6.80 (d, J=8.6 Hz, 2H), 4.53 (dd, J=9.8, 3.4 Hz, 1H), 4.32-4.24 (m, 1H), 4.03 (dd, J=7.9, 5.9 Hz, 1H), 3.96 (s, 2H), 3.77 (s, 3H), 3.57 (td, J=11.4, 2.1 Hz, 1H), 2.98 (d, J=11.6 Hz, 2H), 2.38-2.18 (m, 5H), 2.08 (t, J=11.8 Hz, 2H), 2.02-1.81 (m, 5H), 1.78-1.51 (m, 3H). $^{13}$C NMR (400 MHz, CDCl3): 5161.5, 154.0, 130.6, 129.8, 113.6, 72.0, 68.7, 55.2, 54.9, 46.1, 33.8, 31.9, 29.8, 25.5, 22.9. ESI-MS: m/z 371.2 [M+H]$^+$.

Embodiment 11 Preparing (3-(4-methoxybenzyl)-1-(1-methylpiperidin-4-yl)-1H-1,2,4-triazol-5-yl)methylamine (Compound 11)

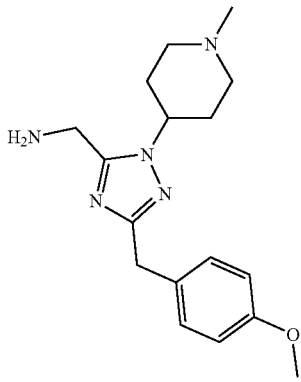 [SMILES: COc1ccc(Cc2nc(CN)n(C3CCN(C)CC3)n2)cc1]

According to the method of embodiment 1, making 2-(tert-butoxycarbonyl)glycine react with 2-(4-methoxyphenyl)thioacetamide shown in formula 1-2 to prepare a thioimide intermediate (53 mg, with the yield of 31%) and then react with 4-hydrazino-1-methylpiperidine to prepare an intermediate product (40 mg, with the yield of 61%), and then removing the tert-butoxycarbonyl protection group with the 1,4-dioxane solution of hydrogen chloride to prepare compound 11 (12 mg, with the yield of 42%), pale yellow oil.

$^1$H NMR (400 MHz, CDCl$_3$): δ 7.25 (d, J=8.6 Hz, 2H), 6.82 (d, J=8.6 Hz, 2H), 4.15-4.09 (m, 1H), 3.95 (s, 2H), 3.93 (s, 2H), 3.77 (s, 3H), 3.48 (s, 1H), 3.03 (d, J=11.4 Hz, 2H), 2.35 (s, 3H), 2.30-2.16 (m, 4H), 1.94-1.91 (m, 4H). $^{13}$C NMR (400 MHz, CDCl3): δ 161.7, 158.1, 155.2, 130.4, 129.8, 113.7, 54.9, 50.7, 45.9, 37.6, 33.9, 31.6. ESI-MS: m/z 316.1 [M+H]$^+$.

Embodiment 12 Preparing 1,3-bis(4-methoxybenzyl)-5-(tetrahydro-2H-pyran-2-yl)-1H-1,2,4-triazole (Compound 12)

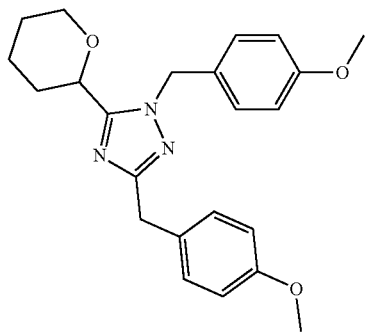 [SMILES: COc1ccc(Cc2nc(C3CCCCO3)n(Cc3ccc(OC)cc3)n2)cc1]

According to the method of embodiment 1, making tetrahydropyran-2-carboxylic acid react with 2-(4-methoxyphenyl)thioacetamide shown in formula 1-2 to prepare a thioimide intermediate (300 mg, with the yield of 26%) and then react with 4-methoxybenzyl hydrazine dihydrochloride to prepare compound 12 (110 mg, with the yield of 67%), pale yellow oil.

$^1$H NMR (400 MHz, CDCl$_3$): δ 7.24 (d, J=8.6 Hz, 2H), 6.80 (d, J=8.6 Hz, 2H), 4.53 (dd, J=9.8, 3.4 Hz, 1H), 4.28 (ddd, J=11.4, 7.3, 4.3 Hz, 1H), 4.05-4.02 (m, 1H), 3.96 (s, 2H), 3.77 (s, 3H), 3.57 (td, J=11.4, 2.1 Hz, 1H), 2.98 (d, J=11.6 Hz, 2H), 2.32 (s, 3H), 2.30-2.23 (m, 2H), 2.11-2.05 (m, 2H), 2.00-1.83 (m, 5H), 1.71-1.57 (m, 3H). $^{13}$C NMR (400 MHz, CDCl$_3$): δ 161.5, 157.9, 154.0, 130.6, 129.8, 113.6, 72.0, 68.7, 55.7, 55.2, 54.9, 54.88, 46.1, 33.8, 31.9, 29.8, 25.5, 22.9. ESI-MS: m/z 394.2 [M+H]$^+$.

Embodiment 13 Preparing 2-(1-(4-methoxybenzyl)-3-phenyl-1H-1,2,4-triazol-5-yl)morpholine (Compound 13)

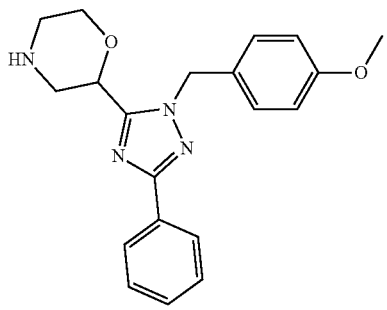 [SMILES: COc1ccc(Cn2nc(-c3ccccc3)nc2C2CNCCO2)cc1]

According to the method of embodiment 1, making 4-(tert-butoxycarbonyl)morpholine-2-carboxylic acid shown in formula 1-1 react with 2-phenylmethanethioamide to prepare a thioimide intermediate (217 mg, with the yield of 62%) and then react with 4-methoxybenzyl hydrazine dihydrochloride to prepare an intermediate product (33 mg, with the yield of 60%), and then removing the tert-butoxycarbonyl protection group with the 1,4-dioxane solution of hydrogen chloride to prepare compound 13 (14.1 mg, with the yield of 56%), pale yellow oil.

$^1$H NMR (400 MHz, CDCl$_3$): δ 8.09 (d, J=7.0 Hz, 2H), 7.49-7.32 (m, 3H), 7.25 (d, J=8.7 Hz, 2H), 6.86 (d, J=8.6 Hz, 2H), 5.63-5.26 (m, 2H), 4.65 (dd, J=7.9, 3.4 Hz, 1H), 3.95-3.59 (m, 5H), 3.30-3.19 (m, 2H), 3.01-2.90 (m, 2H). $^{13}$C NMR (400 MHz, CDCl3): δ 160.7, 159.4, 153.2, 131.0, 129.1, 129.0, 128.4, 127.8, 126.3, 114.1, 70.2, 67.0, 55.2, 52.4, 48.4, 45.4, 29.7. ESI-MS: m/z 351.2 [M+H]$^+$.

Embodiment 14 Preparing 2-(3-benzyl-1-(1-methylpiperidin-4-yl)-1H-1,2,4-triazol-5-yl)morpholine (Compound 14) Hydrochloride

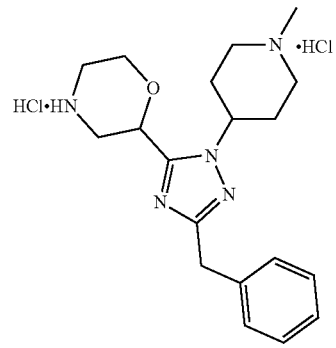

According to the method of embodiment 1, making 4-(tert-butoxycarbonyl)morpholine-2-carboxylic acid shown in formula 1-1 react with 2-phenylthioacetamide to prepare a thioimide intermediate (73 mg, with the yield of 40%) and then react with 4-hydrazino-1-methylpiperidine to prepare an intermediate product (75 mg, with the yield of 85%), and then removing the tert-butoxycarbonyl protection group with the 1,4-dioxane solution of hydrogen chloride to prepare compound 14 hydrochloride (60 mg, with the yield of 79%), white solid powder.

$^1$H NMR (400 MHz, CD3OD) δ 6.98-6.87 (m, 5H), 6.58-6.54 (m, 1H), 5.22-5.19 (m, 1H), 4.75-4.70 (m, 2H), 3.93-3.81 (m, 3H), 3.75 (s, 3H), 3.67-3.54 (m, 6H), 3.40-3.35 (m, 3H), 2.96 (s, 3H), 2.51-2.26 (m, 5H). $^{13}$C NMR (400 MHz, CD3OD): δ 173.4, 161.6, 157.8, 137.8, 130.4, 129.9, 129.8, 129.6, 127.9, 114.8, 68.1, 67.2, 65.0, 58.3, 54.5, 54.21, 54.15, 45.6, 43.9, 34.4, 30.7, 30.2. ESI-MS: m/z 342.1 [M+H]$^+$.

Embodiment 15 Preparing 2-(1-(1-methylpiperidin-4-yl)-3-phenyl-1H-1,2,4-triazol-5-yl)morpholine (Compound 15) Hydrochloride

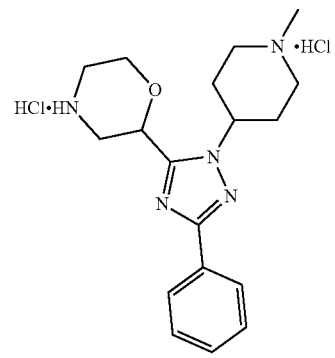

According to the method of embodiment 1, making 4-(tert-butoxycarbonyl)morpholine-2-carboxylic acid shown in formula 1-1 react with 2-phenylmethanethioamide to prepare a thioimide intermediate (217 mg, with the yield of 62%) and then react with 4-hydrazino-1-methylpiperidine to prepare an intermediate product (194 mg, with the yield of 73%), and then removing the tert-butoxycarbonyl protection group with the 1,4-dioxane solution of hydrogen chloride to prepare compound 15 hydrochloride (40 mg, with the yield of 50%), white solid powder.

$^1$H NMR (400 MHz, CD3OD): δ 7.89 (brs, 2H), 7.28 (brs, 3H), 5.37 (s, 1H), 4.12-4.0 (m, 2H), 3.61-2.81 (m, 13H), 2.52-2.16 (m, 4H). $^{13}$C NMR (400 MHz, CD3OD): δ 161.6, 152.4, 131.0, 130.9, 129.8, 127.5, 68.1, 67.3, 64.9, 54.6, 54.2, 45.8, 44.1, 31.1, 30.4. ESI-MS: m/z 328.1 [M+H]$^+$.

Embodiment 16 Preparing 2-(1-(1-methylpiperidin-4-yl)-3-(p-methylphenyl)-1H-1,2,4-triazol-5-yl)morpholine (Compound 16) Hydrochloride According to the method of embodiment 1, making 4-(tert-butoxycarbonyl)morpholine-2-carboxylic acid shown in formula 1-1 react with 2-(4-methylphenyl)methanethioamide to prepare a thioimide intermediate (180 mg, with the yield of 60%) and then react with 4-hydrazino-1-methylpiperidine to prepare an intermediate product (150 mg, with the yield of 71%), and then removing the tert-butoxycarbonyl protection group with the 1,4-dioxane solution of hydrogen chloride to prepare compound 16 hydrochloride (55 mg, with the yield of 76%), white solid powder.

$^1$H NMR (400 MHz, CD3OD): δ 7.93 (d, J=8.0 Hz, 2H), 7.27 (d, J=8.0 Hz, 2H), 6.90 (dd, J=7.8, 5.7 Hz, 1H), 5.50 (d, J=5.9 Hz, 1H), 5.08-5.02 (m, 1H), 4.34-4.03 (m, 2H), 3.90-3.54 (m, 5H), 3.54-3.21 (m, 5H), 2.96 (s, 2H), 2.76-2.20 (m, 6H). $^{13}$C NMR (400 MHz, CD3OD): δ 161.8, 152.4, 141.3, 130.4, 127.4, 114.8, 68.1, 67.1, 64.5, 55.5, 54.5, 54.4, 54.1, 45.7, 44.0, 43.9, 31.1, 30.4, 21.4. ESI-MS: m/z 342.1 [M+H]$^+$.

Embodiment 17 Preparing 2-(1-(1-methylpiperidin-4-yl)-3-(m-methylphenyl)-1H-1,2,4-triazol-5-yl)morpholine (Compound 17) Hydrochloride

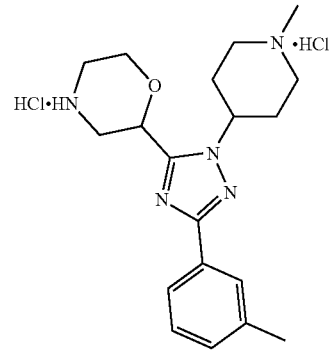

According to the method of embodiment 1, making 4-(tert-butoxycarbonyl)morpholine-2-carboxylic acid shown in formula 1-1 react with 2-(3-methylphenyl)methanethioamide to prepare a thioimide intermediate (185 mg, with the yield of 62%) and then react with 4-hydrazino-1-methylpiperidine to prepare an intermediate product (140 mg, with the yield of 68%), and then removing the tert-butoxycarbonyl protection group with the 1,4-dioxane solution of hydrogen chloride to prepare compound 17 hydrochloride (70 mg, with the yield of 97%), white solid powder.

$^1$H NMR (400 MHz, CD3OD): δ 8.03-7.72 (m, 2H), 7.34-7.24 (m, 3H), 5.46 (dd, J=8.1, 4.2 Hz, 1H), 5.22-4.98 (m, 1H), 4.27-4.10 (m, 2H), 3.96-3.52 (m, 5H), 3.52-3.33 (m, 4H), 2.97 (s, 3H), 2.62-2.18 (m, 6H). $^{13}$C NMR (400 MHz, CD3OD): δ 162.2, 152.5, 139.5, 131.4, 129.6, 127.9, 124.5, 114.8, 68.1, 67.1, 64.4, 58.3, 54.5, 53.9, 45.6, 44.0, 43.9, 31.1, 30.4, 21.4, 20.5, 18.4. ESI-MS: m/z 342.1 [M+H]$^+$.

Embodiment 18 Preparing 4-(5-cyclohexyl-3-(4-methoxybenzyl)-1H-1,2,4-triazol-5-yl)-1-methylpiperidin (Compound 18)

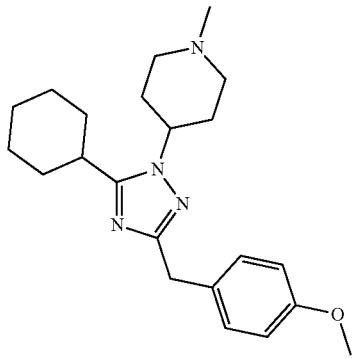 [SMILES: COc1ccc(Cc2nc(C3CCCCC3)n(C3CCN(C)CC3)n2)cc1]

Step 1: Preparing N-(2-(4-methoxyphenyl)ethanethioyl)cyclohexylformamide (Compound 18-2)

A reaction equation is as follows:

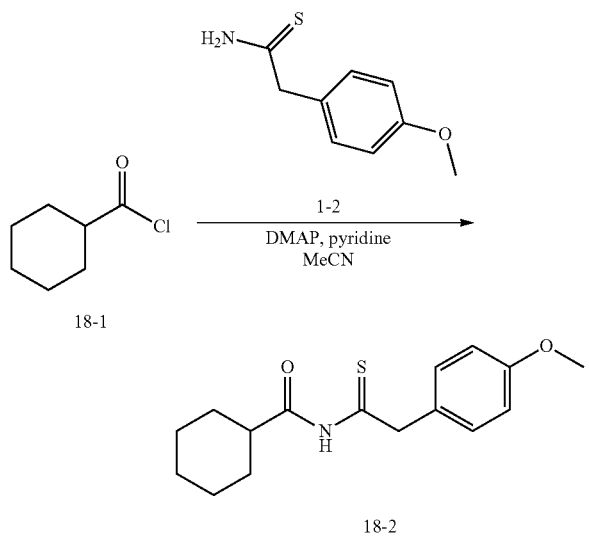

Dissolving 2-(4-methoxyphenyl)thioacetamide (1.0 mmol, 181 mg) shown in formula 1-2,4-dimethylaminopyridine (DMAP, 0.1 mmol, 12 mg) and pyridine (0.15 mmol, 12 mg) in 8 mL of dry acetonitrile, and dropping cyclohexanecarboxylic acid chloride (1.1 mmol, 161 mg) shown in formula 18-1 into the above system under the protection of nitrogen in a room-temperature water bath for reaction at room temperature for 1 day. Diluting the reaction solution with 50 mL of ethyl acetate, cleaning with 20 mL of water and saturated ammonium chloride solution in sequence, drying with anhydrous sodium sulfate, concentrating the ethyl acetate, and then carrying out column chromatography separation [V(petroleum ether):V(ethyl acetate)=8:1-6:1] to obtain 134 mg of pale yellow oil 18-2, with the yield of 46%.

Step 2: Preparing 4-(5-cyclohexyl-3-(4-methoxybenzyl)-1H-1,2,4-triazol-5-yl)-1-methylpiperidin (Compound 18)

A reaction equation is as follows:

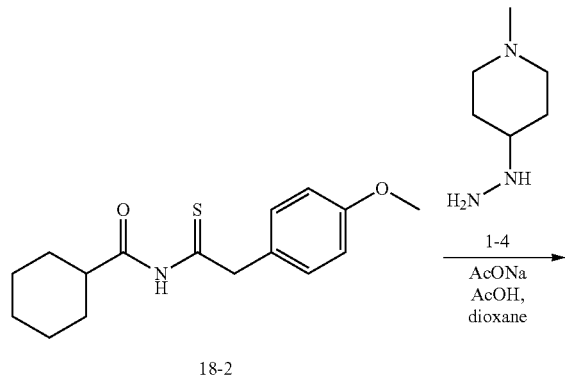

Dissolving the compound 18-2 (0.42 mmol, 122 mg), 4-hydrazino-1-methylpiperidine (0.5 mmol, 65 mg) shown in formula 1-4, and sodium acetate (0.5 mmol, 41 mg) in a mixed solvent of 2 mL of acetic acid and 2 mL of 1,4-dioxane, then sealing, and heating at 80° C. for reaction till the complete reaction of the compound 18-2. Diluting the reaction solution with 50 mL of ethyl acetate, cleaning with 40 mL of saturated sodium carbonate solution and saturated sodium chloride solution in sequence, drying with anhydrous sodium sulfate, conducting concentration, and then carrying out column chromatography separation [V(dichloromethane solution of ammonia):V(methanol)=25:1-20:1] to obtain 100 mg of pale yellow oil 18, with the yield of 65%.

$^1$H NMR (400 MHz, CDCl$_3$) δ 7.27-7.25 (m, 2H), 6.82-6.80 (m, 2H), 3.95 (s, 3H), 3.77 (s, 3H), 3.02-3.00 (m, 2H), 2.68-2.63 (m, 1H), 2.34 (s, 3H), 2.31-2.11 (m, 4H), 1.86-1.64 (m, 9H), 1.38-1.25 (m, 4H). $^{13}$C NMR (400 MHz, CDCl3): δ 161.5, 159.1, 158.1, 130.9, 130.0, 113.7, 55.3, 54.9, 46.2, 35.5, 32.1, 31.9, 26.3, 25.7. ESI-MS: m/z 369.3 [M+H]$^+$.

Embodiment 19 Preparing 4-(5-(tert-butyl)-3-(4-methoxybenzyl)-1H-1,2,4-triazol-5-yl)-1-methylpiperidin (Compound 19)

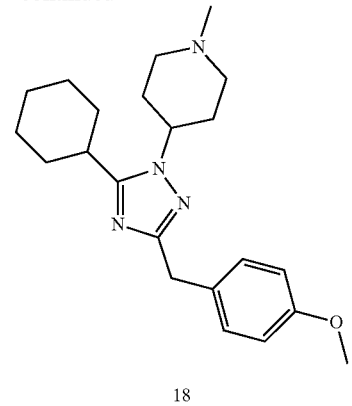

According to the method of embodiment 18, making pivaloyl chloride react with 2-(4-methoxyphenyl)thioacetamide to prepare a thioimide intermediate (20 mg, with the yield of 23%) and then react with 4-hydrazino-1-methylpiperidine to prepare compound 19 (10 mg, with the yield of 49%), pale yellow oil.

$^1$H NMR (400 MHz, CDCl$_3$): δ 7.28 (d, J=9.6 Hz, 2H), 6.81 (d, J=8.6 Hz, 2H), 4.20 (s, 1H), 3.94 (s, 2H), 3.78 (s, 3H), 3.00 (d, J=11.0 Hz, 2H), 2.44-2.25 (m, 5H), 2.18-1.98 (m, 2H), 1.82 (d, J=9.5 Hz, 2H), 1.41 (s, 9H). $^{13}$C NMR (400 MHz, CDCl3): δ 161.3, 160.5, 158.1, 130.8, 130.1, 113.7, 55.4, 46.3, 33.9, 32.4, 32.2, 29.6. ESI-MS: m/z 342.2 [M+H]$^+$.

Embodiment 20 Preparing 4-(3-(4-methoxybenzyl)-5-methyl-1H-1,2,4-triazol-5-yl)-1-methylpiperidin (Compound 20)

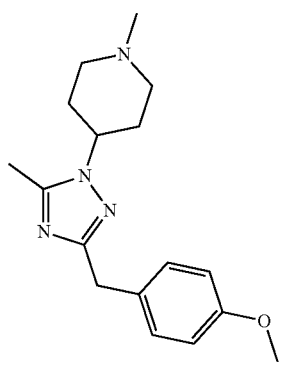

Step 1: Preparing N-(2-(4-methoxyphenyl)ethanethioyl)acetamide (Compound 20-1)

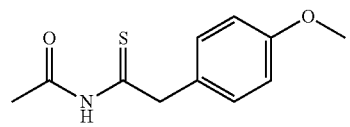

20-1

Dissolving 2-(4-methoxyphenyl)thioacetamide (1.0 mmol, 181 mg) shown in formula 1-2,4-dimethylaminopyridine (0.1 mmol, 12 mg) and pyridine (0.15 mmol, 12 mg) in 8 mL of dry acetonitrile, and dropping cyclohexanecarboxylic acid chloride (1.1 mmol, 161 mg) shown in formula 18-1 into the above system under the protection of nitrogen in a room-temperature water bath for reaction at room temperature for 1 day. Diluting the reaction solution with 50 mL of ethyl acetate, cleaning with 20 mL of water and saturated ammonium chloride solution in sequence, drying with anhydrous sodium sulfate, concentrating the reaction solution, and then carrying out column chromatography separation [V(petroleum ether):V(ethyl acetate)=8:1-6:1] to obtain 38 mg of pale yellow oil 20-1, with the yield of 17%.

Step 2: Preparing 4-(3-(4-methoxybenzyl)-5-methyl-1H-1,2,4-triazol-5-yl)-1-methylpiperidin (Compound 20)

Dissolving the compound 20-1 (0.16 mmol, 36 mg), 4-hydrazino-1-methylpiperidine (0.19 mmol, 25 mg) and sodium acetate (0.2 mmol, 16 mg) in a mixed solvent of 1 mL of acetic acid and 1 mL of 1,4-dioxane, then sealing, and heating at 80° C. for reaction till the complete reaction of the compound 20-1. Diluting the reaction solution with 20 mL of ethyl acetate, cleaning with 20 mL of saturated sodium carbonate solution and saturated sodium chloride solution in sequence, drying with anhydrous sodium sulfate, concentrating the reaction solution, and then carrying out column chromatography separation [V(dichloromethane solution of ammonia):V(methanol)=25:1-20:1] to obtain 16 mg of pale yellow oil 20, with the yield of 33%.

$^1$H NMR (400 MHz, CDCl$_3$): δ 7.25 (d, J=8.7 Hz, 2H), 6.82 (d, J=8.6 Hz, 2H), 4.03-3.88 (m, 3H), 3.77 (s, 3H), 3.05 (s, 2H), 2.39 (s, 3H), 2.36 (m, 3H), 2.31-2.11 (m, 4H), 1.91 (s, 2H). $^{13}$C NMR (400 MHz, CDCl3): δ 161.8, 158.2, 151.4, 130.7, 129.9, 113.9, 55.4, 54.7, 46.1, 34.0, 31.6, 29.8, 12.3. ESI-MS: m/z 301.1 [M+H]$^+$.

Embodiment 21 Preparing 5-cyclohexyl-1,3-dis(4-methoxybenzyl)-1H-1,2,4-triazole (Compound 21)

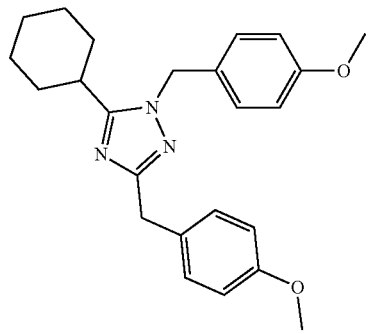 [SMILES: COc1ccc(Cc2nc(C3CCCCC3)n(Cc3ccc(OC)cc3)n2)cc1]

According to the method of embodiment 18, making the compound 18-2 react with (4-methoxybenzyl) hydrazine dihydrochloride to prepare compound 21 (25 mg, with the yield of 45%), pale yellow oil.

$^1$H NMR (400 MHz, CDCl$_3$): δ 7.25 (d, J=8.5 Hz, 2H), 7.08 (d, J=8.5 Hz, 2H), 6.84 (dd, J=11.8, 8.6 Hz, 4H), 5.19 (s, 2H), 4.00 (s, 2H), 3.79 (s, 3H), 3.77 (s, 3H), 2.63 (td, J=11.0, 5.6 Hz, 1H), 1.80-1.78 (m, 2H), 1.73-1.57 (m, 5H), 1.34-1.23 (m, 4H). $^{13}$C NMR (400 MHz, CDCl3): δ 162.1, 160.2, 159.4, 158.2, 130.7, 129.9, 128.4, 128.3, 114.3, 114.2, 113.9, 55.4, 55.3, 51.2, 35.7, 33.9, 31.5, 26.2, 25.6. ESI-MS: m/z 392.2 [M+H]$^+$.

Experiment Example 1 SET8 Lysine Methyltransferase Inhibitor Inhibits the Activity of Lysine Methyltransferase SET8 In Vitro The steps of activity detection are completely based on the SET8 methyltransferase inhibitor screening assay kit of Cayman Company. In short, reagents in the kit are added to the 96-well plate to be tested according to the Table A below.

TABLE A

|  | Mixed Liquor | Polypeptide | Buffer Solution | Inhibitor |
|---|---|---|---|---|
| Initial Activity | 100 μL | 10 μL | 5 μL | / |
| Background | 100 μL | 10 μL | 5 μL | / |
| Sample | 100 μL | 10 μL | / | 5 μL |

Then 10 μL of SET8 albumen protein is added to each well, and the reaction begins. After incubation at 37° C. for 10 min, the fluorescence intensity (A) value is measured at the excitation wavelength of 535 nm and the absorption wavelength of 590 nm. the inhibition rate of the compound is calculated according to the following formula: Inhibition rate %=($A_{normal}$−$A_{sample}$)/)Normal*100%, and the inhibition rate of each inhibitor on lysine methyltransferase is shown in Table 1.

TABLE 1

Inhibition Rate of Each Inhibitor on Lysine Methyltransferase

| Compound | Inhibition Rate (%) |
|---|---|
| 1 | 58.4 |
| 2 | 74.2 |
| 3 | 70.0 |
| 4 | 71.5 |
| 5 | 70.2 |
| 6 | 70.3 |
| 7 | 70.8 |
| 8 | 69.3 |
| 9 | 72.3 |
| 10 | 43.6 |
| 11 | 36.8 |
| 12 | 67.8 |
| 13 | 32.5 |
| 14 | 59.2 |
| 15 | 53.9 |
| 16 | 54.8 |
| 17 | 58.3 |
| 18 | 43.8 |
| 19 | 45.2 |
| 20 | 76.9 |
| 21 | 43.7 |

The result shows that the SET8 lysine methyltransferase provided by the present invention has a significant inhibiting effect on lysine methyltransferase SET8.

Experiment Example 2 Research on Anti-Tumor Activity of SET8 Lysine Methyltransferase Inhibitor 1. Experimental Method: Glioma cell line SH-SY5Y, colorectal cancer cell line SW480 and liver cancer cell line HepG2 are respectively cultured in an RPMI-1640 medium containing 10% calf serum at 37° C. in a 5% $CO_2$ incubator. The CCK-9 method is adopted for cell proliferation inhibition test, and the main operation is as follows: taking the tumor cell line in the logarithmic phase, digesting with 0.25% trypsin, preparing an RPMI-1640 medium containing 10% newborn calf serum into a cell suspension of $6 \times 10^4$ cells/mL, and inoculating the cell suspension into a 96-well plate, with 100 μL per well. Culturing at 37° C. and 5% $CO_2$ saturated humidity for 12 h. After adherence, absorbing the culture supernatants in the wells, and adding the sample solution prepared from the RPMI-1640 medium containing 1% calf serum to each well so that the final concentrations of the samples are 100 μM, 30 μM, 10 μM, 3 μM, 1 μM, and 0.3 μM respectively. With 3 wells in parallel for each concentration, continuing culturing for 48 h, then adding 10 μL of CCK-8 solution (Dalian Meilun, MA0218) to each well, and continuing incubating at 37° C. and 5% $CO_2$ for 4 h. Selecting 470 nm on the enzyme-linked immunosorbent assay apparatus to measure the light absorption value of each well, and setting a blank group (only adding a culture solution containing cells) and a control group (using the culture solution to replace drugs) to calculate the cell proliferation inhibition rate. Inhibition rate (%)=(1−average OD value of 3 wells in experimental group/average OD value of 3 wells in control group)×100%. With the inhibition rate as an ordinate, a regression curve is drawn to calculate the $IC_{50}$ value of the sample. Graphpad prism 7.0 software are adopted for data processing and statistical analysis by.

2. Experimental Result of Anti-tumor Activity

The results of $IC_{50}$ and IC % for 100 μM of each inhibitor on the selected glioma cell line SH-SY5Y, colorectal cancer cell line SW480 or liver cancer cell line HepG2 are shown in Table 2.

TABLE 2

Anti-tumor Activity of SET8 Lysine Methyltransferase Inhibitor

| | SH-SY5Y | | SW480 | | HepG2 | |
|---|---|---|---|---|---|---|
| Compound | $IC_{50}$ (μM) | IC % for 100 μM | $IC_{50}$ (μM) | IC % for 100 μM | $IC_{50}$ (μM) | IC % for 100 μM |
| 1 | 94.7 | 52.5 | — | — | — | — |
| 2 | 13.7 | 78.3 | 16.4 | 75.8 | 17.6 | 51.5 |
| 3 | 22.62 | 76.5 | 18.3 | 73.2 | 19.2 | 48.8 |
| 4 | 78.6 | 57.8 | — | — | — | — |
| 5 | 81.3 | 57.1 | — | — | — | — |
| 6 | 76.5 | 58.6 | — | — | — | — |
| 7 | 78.4 | 57.9 | — | — | — | — |
| 8 | 73.1 | 59.5 | — | — | — | — |
| 9 | 77.3 | 58.5 | — | — | — | — |
| 10 | 122.9 | 43.3 | — | — | — | — |
| 11 | 132.3 | 39.9 | — | — | — | — |
| 12 | 71.8 | 60.1 | — | — | — | — |
| 13 | 138.2 | 37.8 | — | — | — | — |
| 14 | 92.5 | 53.2 | — | — | — | — |
| 15 | 95.3 | 52.3 | — | — | — | — |
| 16 | 93.7 | 52.8 | — | — | — | — |
| 17 | 92.1 | 53.7 | — | — | — | — |
| 18 | 126.4 | 41.9 | — | — | — | — |
| 19 | 117.6 | 44.8 | — | — | — | — |
| 20 | 10.4 | 84.7 | 11.3 | 79.6 | 13.6 | 68.7 |
| 21 | 113.5 | 46.2 | — | — | — | — |

"—" indicates no test.

It can be seen from the table that each compound shows good tumor cell proliferation inhibitory activity on the glioma cell line SH-SY5Y and the compounds 2, 3 and the compound 20 show good tumor cell proliferation inhibitory activity on the colorectal cancer cell line SW480 or the liver cancer cell line HepG2.

We claim:
1. A composition, comprising:
a compound selected from the group consisting of:
1): 2-(3-(4-methoxybenzyl)-1-(1-methylpiperidin-4-yl)-1H-1,2,4-triazol-5-yl) morpholine;
2): 2-(1,3-bis(4-methoxybenzyl)-1H-1,2,4-triazol-5-yl) morpholine;
3): 2-(1-cyclohexyl-3-(4-methoxybenzyl)-1H-1,2,4-triazol-5-yl) morpholine;
4): 2-(3-(4-methoxybenzyl)-1-phenyl-1H-1,2,4-triazol-5-yl) morpholine;
5): 2-(3-(4-methoxybenzyl)-1-(m-methylphenyl)-1H-1,2,4-triazol-5-yl) morpholine;
6): 2-(3-(4-methoxybenzyl)-1-(pyridin-2-yl)-1H-1,2,4-triazol-5-yl) morpholine;
7): 2-(3-(4-methoxybenzyl)-1-(pyrazin-2-yl)-1H-1,2,4-triazol-5-yl) morpholine;
8): 2-(3-(4-methoxybenzyl)-1-methyl-1H-1,2,4-triazol-5-yl) morpholine;
9): 4-benzyl-2-(3-(4-methoxybenzyl)-1-(1-methylpiperidin-4-yl)-1H-1,2,4-triazol-5-yl) morpholine;
10): 4-(4-methoxybenzyl)-5-(tetrahydro-2H-pyran-2-yl)-1H-1,2,4-triazol-5-yl)-1-methylpiperidin;
11): 3-(4-methoxybenzyl)-1-(1-methylpiperidin-4-yl)-1H-1,2,4-triazol-5-yl)methylamine;

12): 1,3-bis(4-methoxybenzyl)-5-(tetrahydro-2H-pyran-2-yl)-1H-1,2,4-triazole;
13): 2-(1-(4-methoxybenzyl)-3-phenyl-1H-1,2,4-triazol-5-yl) morpholine;14): 2-(3-benzyl-1-(1-methylpiperidin-4-yl)-1H-1,2,4-triazol-5-yl) morpholine;
15): 2-(1-(1-methylpiperidin-4-yl)-3-phenyl-1H-1,2,4-triazol-5-yl) morpholine;
16): 2-(1-(1-methylpiperidin-4-yl)-3-(p-methylphenyl)-1H-1,2,4-triazol-5-yl) morpholine;
17): 2-(1-(1-methylpiperidin-4-yl)-3-(m-methylphenyl)-1H-1,2,4-triazol-5-yl) morpholine;
18): 4-(5-cyclohexyl-3-(4-methoxybenzyl)-1H-1,2,4-triazol-5-yl)-1-methylpiperidin;
19): 4-(5-(tert-butyl)-3-(4-methoxybenzyl)-1H-1,2,4-triazol-5-yl)-1-methylpiperidin;
20): 4-(3-(4-methoxybenzyl)-5-methyl-1H-1,2,4-triazol-5-yl)-1-methylpiperidin; and
21): 5-cyclohexyl-1,3-[d]bis(4-methoxybenzyl)-1H-1,2,4-triazole.

2. A pharmaceutical composition as an SET8 lysine methyltransferase inhibitor, comprising
a compound of claim 1; and
a pharmaceutically acceptable carrier or excipient.

* * * * *